United States Patent [19]
Arcari et al.

[11] 3,957,785
[45] May 18, 1976

[54] Bβ-PYRIMIDINO-AMINOMETHYL-10α-ERGOLINE AND 10α-METHOXYERGOLINE DERIVATIVES

[75] Inventors: Giuliana Arcari; Luigi Bernardi, both of Milan; Germano Bosisio, Palazzolo Milanese; Maurizio Foglio, Milan; Alfredo Glasser, Milan; Aldemio Temperilli, Milan, all of Italy

[73] Assignee: Societa' Farmaceutici Italia S.p.A., Milan, Italy

[22] Filed: July 31, 1974

[21] Appl. No.: 493,335

Related U.S. Application Data

[63] Continuation-in-part of Ser. No. 310,801, Nov. 30, 1972, abandoned.

[30] Foreign Application Priority Data

Dec. 2, 1971  Italy.................................. 31932/71

[52] U.S. Cl.................. 260/256.4 C; 260/256.4 N; 424/251
[51] Int. Cl.².......................................... C07D 457/02
[58] Field of Search............... 260/256.4 C, 256.4 N

[56] References Cited
UNITED STATES PATENTS

| | | | |
|---|---|---|---|
| 2,449,908 | 9/1948 | Prevost | 260/251 |
| 2,484,606 | 10/1949 | Braker | 260/239.6 |
| 3,557,118 | 1/1971 | Arcamone et al. | 260/285.5 |
| 3,646,046 | 2/1972 | Arcamone et al. | 260/256.4 B |
| 3,681,349 | 8/1972 | Schwan et al. | 260/256.4 C |

OTHER PUBLICATIONS

Sidgwick, *Organic Chemistry of Nitrogen*, Oxford Press, 1937, pp. 297–298.

*Primary Examiner* — Alton D. Rollins
*Assistant Examiner* — James H. Turnipseed
*Attorney, Agent, or Firm* — Hubbell, Cohen, Stiefel & Gross

[57] ABSTRACT

Novel 8β-pyrimidino-aminomethyl-10α-ergoline and 10α-methoxyergoline derivatives which possess a high and prolonged adrenolytic activity and a low toxicity, and some of which also possess hypotensive and analgesic activity are prepared by reacting a pyrimidine anion with an ergoline derivative in an aprotic solvent.

22 Claims, No Drawings

8β-PYRIMIDINO-AMINOMETHYL-10α-ERGOLINE AND 10α-METHOXYERGOLINE DERIVATIVES

CROSS REFERENCE TO RELATED APPLICATIONS

This application is a continuation-in-part of co-pending application, Ser. No. 310,801, filed Nov. 30, 1972, now abandoned, the contents of which are expressly incorporated herein by reference.

BACKGROUND OF THE INVENTION

1. Field of the Invention

The present invention relates to new adrenolytic ergoline derivatives.

2. Description of the Prior Art

Dihydrolysergamine and 1-methyl-dihydrolysergamine, the starting materials for the preparation of the compounds of the invention are known substances and are described in the literature at Gazz.Chim.Ital., 94, (1964), p 936.

SUMMARY OF THE INVENTION

The present invention provides a new class of 8β-pyrimidino-aminomethyl-10 α-ergoline and 10 α-methoxyergoline derivatives of the formula (I):

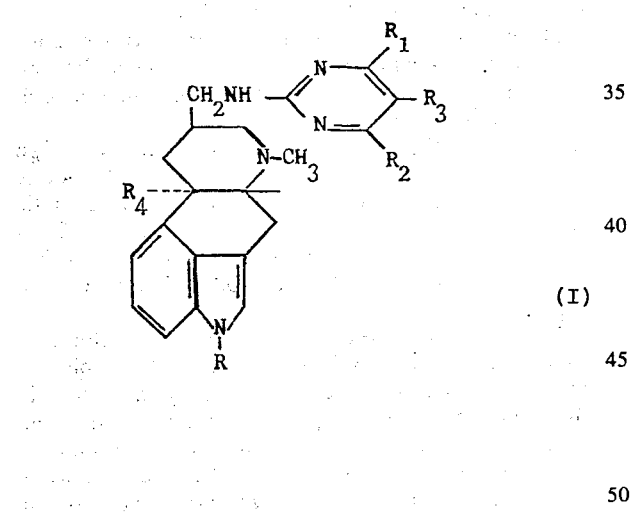

(I)

wherein R is hydrogen or methyl; $R_1$ and $R_2$ are independently selected from the group consisting of hydrogen, alkyl groups having 1 to 6 carbon atoms, methoxy and phenyl; $R_3$ is hydrogen, halogen, an alkyl group having 1 to 6 carbon atoms, an alkoxy group having 1 to 6 carbon atoms, phenyl, cyano, nitro, amino, an acylamino group having 1 to 3 carbon atoms, a carboxamido group having 1 to 3 carbon atoms or a carbalkoxy group having 1 to 3 carbon atoms; and $R_4$ is hydrogen or methoxy.

These compounds of formula (I) are prepared by a process having as its starting materials the known compounds dihydrolysergamine and 1-methyl-dihydrolysergamine wherein the formation of the intermediate 8β-guanidinomethyl derivative of 6-methyl- and 1,6-dimethyl-10 α-ergoline occurs according to the reaction:

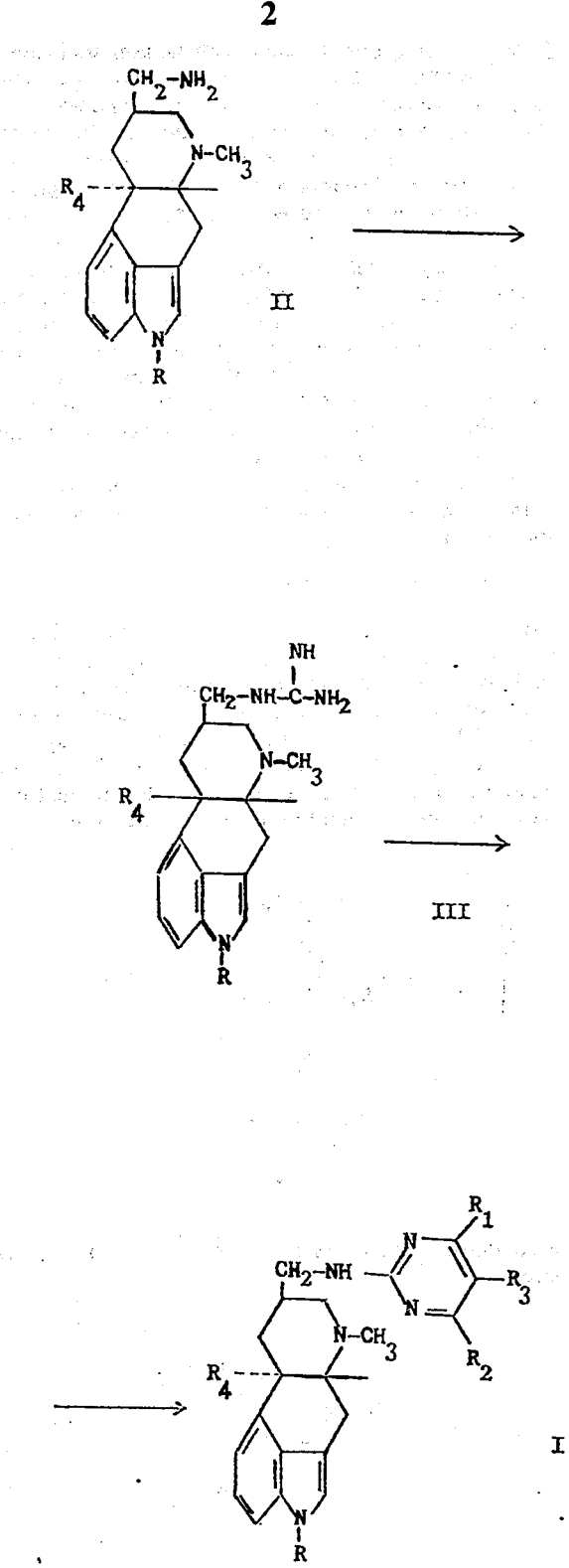

wherein R, $R_1$, $R_2$, $R_3$ and $R_4$ are as defined above. The starting materials, dihydrolysergamine and 1-methyl-dihydrolysergamine (II) are described in the literature (Gazz.Chim.Ital., 94 (1964), p 936).

The intermediate 6-methyl- or 1,6-dimethyl-8β-guanidinomethyl-10 α-ergoline of formula III is obtained by reacting compound II with a compound capable of transforming the amino group into a guanidino group such as, for example, cyanamide, 1-guanidyl-3,5-dimethyl-pyrazole, an S-alkylisothiourea, wherein the alkyl group has 1–4 carbon atoms, and is preferably, ethyl, an O-alkylisourea, wherein the alkyl group has 1–4 carbon atoms, and is preferably, ethyl, or salts thereof.

This reaction is effected in an organic solvent such as a lower alkanol, preferably, ethanol at an elevated temperature, preferably at the boiling temperature of the solvent, i.e., about 50°–80°C. If the reactant employed is in the form of a salt, the corresponding salt of the 8β-guanidino-methyl derivative thus obtained, is thereafter transformed into the free base by treating with alkali in a conventional manner.

The 8β-guanidinomethyl derivative of the formula III is then condensed with an 8β-dicarbonyl compound of the formula:

R₁—CO—CH(R₃)—CO—R₂ wherein $R_1$, $R_2$ and $R_3$ are as defined above. This reaction is effected in the presence of an organic solvent, such as a lower alkanol, for example, methanol, ethanol, propanol, butanol, etc. at a temperature between 10° and 150°C, over a period of 1 hour to 6 days.

The compounds of the invention can also be prepared by an alternative process. According to this alternative process, an ergoline compound of formula:

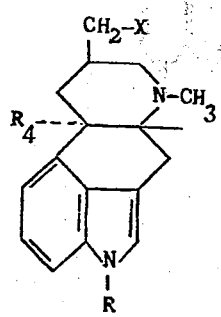

is condensed, in an aprotic solvent with an anion of the structure:

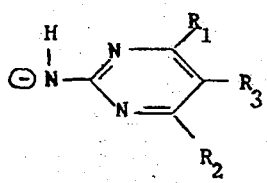

wherein R, $R_1$, $R_2$, $R_3$ and $R_4$ are as defined above, and X is selected from the group consisting of chlorine, bromine, mesyl or tosyl radical.

This anion is obtained by reacting the corresponding 2-aminopyrimidine with an organometallic compound, such as butyllithium, or a strong base such as sodium hydride, potassium hydride, sodium amide or potassium amide.

The pyrimidine anion is prepared directly in the reaction mixture in situ according to the following:

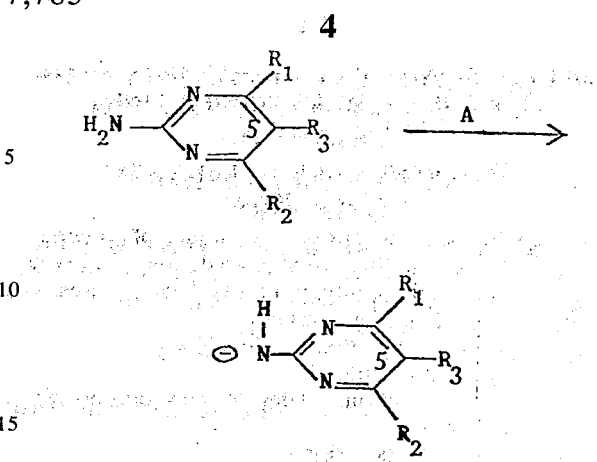

wherein A is the strong base and by using dimethylformamide or liquid ammonia as a solvent. Which strong base is used is determined according to the nature of the group attached to the 5-position of the pyrimidine ring. If an electron attracting group is present in the 5-position (nitro or cyano group), sodium or potassium hydride is preferred; if an electron donor group (methyl) is attached to position 5, sodium or potassium amide will be used.

When this reaction is complete, the ergoline derivative, dissolved in an aprotic solvent, such as dimethylformamide or dimethylsulfoxide, is added and the mixture is heated to a temperature between 50° and 110°C for a period of from 30 minutes to 5 hours.

The obtained 8β-pyrimidino-aminomethyl derivative (I) is isolated and purified by crystallization or chromatography according to known techniques such as column chromatography.

The compounds of the present invention have a high and prolonged adrenolytic activity and a low toxicity and are therefore useful in therapy. This adrenolytic activity was tested on several of the present compounds in vitro in comparison with dihydroergotamine on isolated guinea pig seminal vescicle suspended in a physiological solution.

Table 1 reports the values of concentrations, in μg/ml., which are able to produce a 50% inhibition ($IC_{50}$) of the spasmogen effect caused by adrenaline. In the Table, several of the present compounds are compared with dihydroergotamine and it can be seen from these data that the compounds of the invention are at least twice as effective as dihydroergotamine and in one case, one hundred fifty times as effective as dihydroergotamine.

TABLE I

| Compound | $TC_{50}$ μc/ml |
|---|---|
| 1,6-dimethyl-8β-(5-nitro-2-pyrimidino-aminomethyl)-10α-ergoline | 0.007 |
| 1,6-dimethyl-8β-(2-pyrimidino-aminomethyl)-10α-methoxyergoline | 0.005 |
| 1,6-dimethyl-8β-(5-nitro-2-pyrimidino-aminomethyl)-10α-methoxyergoline | 0.001 |
| 1,6-dimethyl-8β-(5-methyl-2-pyrimidino-aminomethyl)-10α-methoxyergoline | 0.001 |
| 1,6-dimethyl-8β-(5-cyano-2-pyrimidino-aminomethyl)-10α-methoxyergoline | 0.0001 |
| 1,6-dimethyl-8β-(5-cyano-2-pyrimidino-aminomethyl)-10α-ergoline | 0.005 |
| 1,6-dimethyl-8β-(5-bromo-2-pyrimidino-aminomethyl)-10α-methoxyergoline | 0.005 |
| 1,6-dimethyl-8β-(5-methyl-2-pyrimidino-aminomethyl)-10α-ergoline | |
| dihydroergotamine | 0.015 |

The adrenolytic activity of the compounds of the invention was also determined in vivo on the rat in comparison with dihydroergotamine and nicergoline. Table 2 reports the doses in mg/kg ($ID_{50}$) able to reduce by 50% the lethal effects caused by adrenaline after oral (os) and intravenous (i.v.) administration of these compounds as compared with dihydroergotamine and with nicergoline, i.e., 1,6-dimethyl-8 -(5'-bromonicotinoyloxymethyl)-10 -methoxyergoline (Br. J. Pharmac, 34, 700, 1968).

et al. Bioch. Pharmac. 21, 2205, 1972) while the compounds of the present invention, under the same conditions, remain practically unaltered. This greater stability was confirmed by the determination of the submaximal inhibiting dosage which protects 80% of the tested animals (rats) against a single dose of 200 mg/Kg of body weight of adrenalin injected 8 hours after administration of the tested compounds according to the invention.

These data are reported in Table 4, where, for comparative purposes, the corresponding data for dihydroergotamine and nicergoline are given

TABLE 2

| Compound | $ID_{50}$ mg/kg (i.v.) | (os) |
|---|---|---|
| 1,6-dimethyl-8β-(4,6-dimethyl-2-pyrimidino-aminomethyl) 10α-ergoline | — | 1.25 |
| 1,6-dimethyl-8β-(5-nitro-2-pyrimidino-aminomethyl) 10α-ergoline | 0.09 | 0.04 |
| 1,6-dimethyl-8β-(5-amino-2-pyrimidino-aminomethyl)-10α-ergoline | 0.18 | 0.5 |
| 1,6-dimethyl-8β-(5-chloro-2-pyrimidino-aminomethyl)-10α-ergoline | — | 0.14 |
| 1,6-dimethyl-8β-(2-pyrimidino-aminomethyl)-10α-methoxyergoline | 0.2 | 1 |
| 1,6-dimethyl-8β-(5-nitro-2-pyrimidino-aminomethyl)-10α-methoxyergoline | 0.2 | <0.1 |
| 1,6-dimethyl-8β-(5-methyl-2-pyrimidino-aminomethyl)-10α-methoxyergoline | 0.1 | 0.1 |
| 1,6-dimethyl-8β-(5-cyano-2-pyrimidino-aminomethyl)-10α-methoxyergoline | 0.015 | 0.2 |
| 1,6-dimethyl-8β-(5-cyano-2-pyrimidino-aminomethyl)-10α-ergoline | 0.05 | 0.05 |
| 1,6-dimethyl-8β-(5-bromo-2-pyrimidino-aminomethyl)-10α-methoxyergoline | 0.08 | 0.32 |
| 1,6-dimethyl-8β-(5-methyl-2-pyrimidino-aminomethyl)-10α-ergoline | 0.15 | 0.1 |
| dihydroergotamine | 0.08 | 15.0 |
| 1,6-dimethyl-8β-(5'-bromonicotinoyloxymethyl-10α-methoxyergoline (nicergoline) | 0.024 | 7.0 |

TABLE 4

| Compound | ID in mg/kg body weight; peros in rats after 8 hours |
|---|---|
| 1,6-dimethyl-8β-(5-nitro-2-pyrimidino-aminomethyl)-10α-ergoline | 0.5 |
| 1,6-dimethyl)8β-(5-amino-2-pyrimidino-aminomethyl)-10α-ergoline | 1 |
| 1,6-dimethyl)8β-(5-chloro-2-pyrimidino-aminomethyl)-10α-ergoline | 1 |
| 1,6-dimethyl-8β-(5-cyano-2-pyrimidino-aminomethyl)-10αmethoxyergoline | 0.5 |
| dihydroergotamine | >20 |
| 1,6-dimethyl-8β-(5'-bromonicotinoyloxymethyl) 10α-methoxyergoline (nicergoline) | >20 |

Some of the compounds reported in Table 2 have a long lasting effect of up to 24 hours as shown by the data contained in Table 3.

The low toxicity of the compounds of the invention is demonstrated by the data in Table 5 which sets forth the $LD_{50}$ values, both per os and i.v. in rats for several of the compounds of the invention.

TABLE 5

| Compounds | $LD_{50}$ mg/kg i.v. | os |
|---|---|---|
| 1,6-dimethyl-8β-(2-pyrimidino-aminomethyl)-10α-methoxyergoline | 25 | 250 |
| 1,6-dimethyl-8β-(5-nitro-2-pyrimidino-aminomethyl) 10α-methoxyergoline | 28 | 200 |
| 1,6-dimethyl-8β(5-methyl-2-pyrimidino-aminomethyl-10α-methoxyergoline | 18 | — |
| 1,6-dimethyl-8β-(5-cyano-2-pyrimidino-aminomethyl)-10α-methoxyergoline | 38 | 160 |
| 1,6-dimethyl-8β-(5-cyano-2-pyrimidino-aminomethyl)- 10α-ergoline | 25 | 35 |
| 1,6-dimethyl-8β-(5-bromo-2-pyrimidino-aminomethyl)-10α-methoxyergoline | 50 | 230 |
| 1,6-dimethyl-8β-(5-methyl-2-pyrimidino-aminomethyl) 10α-ergoline | 35 | 140 |
| 1,6-dimethyl-8β-(5-amino-2-pyrimidino-aminomethyl)-10α-ergoline | 18 | 140 |

TABLE 3

Percentage of animals protected against lethal adrenaline dose

TABLE 3

| Compound | Dose mg/Kg (peros) | Hours after administration of the compound (% survivors) | | | | | | |
|---|---|---|---|---|---|---|---|---|
| | | 0.5 | 1 | 2 | 4 | 8 | 16 | 24 |
| 1,6-dimethyl-8β-(4,6-dimethyl-2-pyrimidino-aminomethyl-) 10α-ergoline | 2.5 | — | 80 | 60 | 30 | — | — | — |
| | 5 | — | 100 | 80 | 50 | 20 | — | — |
| | 10 | — | 100 | 100 | 60 | — | — | — |
| 1,6-dimethyl-8β-(5-nitro-2-pyrimidino-aminomethyl)-10α-ergoline | 0.1 | 50 | 90 | 60 | 70 | 60 | 10 | — |
| | 0.5 | 100 | 100 | 100 | 90 | 80 | 30 | 20 |
| 1,6-dimethyl-8β-(5-cyano-2-pyrimidino-aminomethyl)-10α-methoxyergoline | 0.2 | — | — | 100 | 90 | — | — | — |
| | 0.5 | — | 80 | 90 | 80 | 80 | — | — |
| 1,6-dimethyl-8β-(5-nitro-2-pyrimidino-aminomethyl)-10α methoxyergolIne | 0.1 | — | 70 | 80 | — | — | — | — |
| | 0.5 | 100 | — | 100 | 90 | 40 | — | — |

Furthermore, nicergoline is known to be rapidly metabolized in the presence of blood in vitro (Arcamone In addition, it has also been found that some of the compounds according to the invention display an unexpected hypotensive, analgesic, antiserotonin and sedative activity. The hypotensive and analgesic data for some of the compounds are given in Table 6.

The hypotensive activity was tested on the hypertensive rat; the reported data being the dose, expressed in mg/kg per os, which causes a pressure drop of about 30–40 mmHg.

The analgesic activity was evaluated by means of the hot plate test and the writhing test, the data being given in comparison with morphine and D-propoxyphene.

TABLE 6

| Compounds | Hypotensive Activity Active Dose mg/kg per os | Analgesic Activity | | | |
|---|---|---|---|---|---|
| | | Hot plate | | Writhing | |
| | | morphine | D-propoxyphene | morphine | D-propoxyphene |
| 1,6-dimethyl-8β-(2-pyrimidino-aminomethyl)-10α-ergoline | 5–10 | 1 | 1 | 0.5 | 5 |
| 1,6-dimethyl-8β-(5-methyl-2-pyrimidino-aminomethyl)-10α-ergoline | 5–10 | 1 | 5 | 0.5 | 5 |
| 1,6-dimethyl-8β(5-cyano-2-pyrimidino-aminommethyl)-10α-methoxyergoline | 1–2.5 | — | — | 0.2 | 1 |
| 1,6-dimethyl-8β-(5-nitro-2-pyrimidino-aminomethyl)-10α-methoxyergoline | 1–2.5 | — | — | — | — |
| 1,6-dimethyl-8β-(5-cyano-2-pyrimidino-aminomethyl)-10α-ergoline | 2.5–5 | — | — | — | — |

In the hot plate and writhing tests, the comparison compounds morphine and D-propoxyphene have been arbitrarily assigned the value of 1. Thus, in the hot plate test, the compound 1,6-dimethyl-8β-(2-pyrimidino-aminomethyl)-10α-ergoline has the same activity as both morphine and D-propoxyphene, while in the writhing test that compound has ½ the activity of morphine and 5 times the activity of D-propoxyphene.

DESCRIPTION OF THE PREFERRED EMBODIMENTS

The following examples are given to illustrate the invention without, however, limiting it.

EXAMPLE 1

1,6-dimethyl-8β-(5-nitro-2-pyrimidino-aminomethyl)-10α-ergoline

A solution of 5 g of 1-methyl-dihydrolysergamine and 4 g of 1-guanyl-3,5-dimethylpyrazole nitrate in 200 ml of ethanol was refluxed for 7 hours. The solution was concentrated until crystallization began and 4 g of 1,6-dimethyl-8β-guandinomethyl-10β-ergoline nitrate melting at 242°–244° C were obtained. To a solution of 3 g of this product in 120 ml of methanol, 4.8 g of the sodium salt of nitromalondialdehyde (Organic Synthesis 27, 60) and 0.1 ml of piperidine were added.

The solution was stirred for 8 hours. The resulting precipitate was then collected with 2.5 g of 1,6-dimethyl-8β-(5-nitro-2-pyrimidino-aminomethyl)-10α-ergoline, melting at 204°–206°C, being obtained.

EXAMPLE 2

1,6-dimethyl-8β(4,6-dimethyl-2-pyrimidino-aminomethyl)-10α-ergoline

A solution of 4 g of 1-methyl-dihydrolysergamine in 150 ml of ethanol was refluxed for 4 hours with 2 equivalents of cyanamide. It was neutralized with nitric acid and concentrated until crystallization began. 2 g of 1,6-dimethyl-8β-guanidinomethyl-10α-ergoline nitrate melting at 242°–244°C were separated.

The corresponding free base was obtained by the addition of an equivalent of sodium methylate to 1,6-dimethyl-8β-guanidinomethyl-10α-ergoline nitrate. 0.9 g of 1,6-dimethyl-8β -guanidinomethyl-10 α-ergoline base in 20 ml of acetylacetone was dissolved and the solution was refluxed for 3 hours. The residue was evaporated and chromatographed on an alumina column using chloroform as the eluant. This solvent was used in all examples in which column chromatography was used to purify the product. 0.6 g of 1,6-dimethyl-8β-(4,6-dimethyl-2-pyrimidinoaminomethyl)-10α-ergoline melting at 129°–131° was obtained.

EXAMPLE 3

1,6-dimethyl-8β-(4-methyl-6-phenyl-2-pyrimidino-aminomethyl)-10 α-ergoline 1 g of 1,6-dimethyl-8β-guanidinomethyl-10α-ergoline base and 5 g of benzoylacetone were heated to 80°C for 65 hours. The reaction mixture was concentrated in vacuo and the residue chromotographed on an alumina column. 0.5 g of 1,6-dimethyl-8β-(4-methyl-6-phenyl-2-pyrimidino-aminomethyl)-10α-ergoline, melting at 192°–194°C, was obtained.

EXAMPLE 4

1,6-dimethyl-8β-(5-chloro-2-pyrimidino-aminomethyl)-10α-ergoline 2 g of 1,6-dimethyl-8β-guanidinomethyl-10α-ergoline base and 2 equivalents of chloromalondiadehyde (J.Chem.Soc. 1949, p. 1550) were heated in butanol at 110°C for 4 hours. The reaction mixture was concentrated in vacuo and the residue was chromatographed on an alumina column. 1.2 g of 1,6-dimethyl-8β-(5-chloro-2-pyrimidino-aminomethyl)-10 α-ergoline, melting at 190°-192°C, were obtained.

EXAMPLE 5

1,6-dimethyl-8β (5-nitro-2-pyrimidino-aminomethyl)-10α-ergoline

One equivalent of 1-methyl-dihydrolysergamine was reacted with one equivalent of S-ethylisothiourea hydrochloride in 80% ethanol at 50°C for 3 hours. The 1,6-dimethyl-8β-guanidinomethyl-10α-ergoline hydrochloride thus obtained was condensed with the sodium salt of nitromalondialdehyde in a 1:1 molar ratio in the same manner as described in Example 1 to obtain the product in a yield of 45%; m.p. 204°–206°C.

EXAMPLE 6

1,6-dimethyl-8β -(5-nitro-2-pyrimidino-aminomethyl)-10α-ergoline

By operating in accordance with the procedures described in Example 5, but using O-ethylisourea hydrochloride in lieu of S-ethylisothiourea, 1,6-dimethyl-8β-guanidinomethyl-10α-ergoline hydrochloride was obtained in a yeild of 49%, m.p. 275°–278°C.

EXAMPLE 7

1,6-dimethyl-8β-(5-bromo-2-pyrimidino-aminomethyl)-10α-ergoline

By operating in accordance with the procedures described in Example 1, using bromomalondialdehyde (J,Org.Chem.28, 1963, p. 3243), 1,6-dimethyl-8β -(5-bromo-2-pyrimidino-aminomethyl)-10α-ergoline melting at 186°C, was obtained in 60% yield.

EXAMPLE 8

6-methyl-8β-(5-nitro-2-pyrimidino-aminomethyl)-10α-ergoline

A solution of dihydrolysergamine and 1-guanyl-3,5-dimethylpyrazole nitrate in ethanol was refluxed for 7 hours. By crystallization from the reaction mixture, 6-methyl-8β-guanidinomethyl-10 α-ergoline nitrate melting at 235°-237°C was obtained. This product was reacted with nitromalondialdehyde as described in Example 1 to obtain 6-methyl-8β-(5-nitro-2-pyrimidino-aminomethyl)-10α -ergoline in 61% yield; m.p. 258°–260°C.

By operating in accordance with the procedures described in Example 1, the following compounds were prepared:

1,6-dimethyl-8β-(2-pyrimidino-aminomethyl)-10α-ergoline; m.p. 164°–166°C
1,6-dimethyl-8β-(5-phenyl-2-pyrimidino-aminomethyl)-10α-ergoline; m.p. 185°C
1,6-dimethyl-8β-(5-methoxy-2-pyrimidino-aminomethyl)-10α-ergoline; m.p. 171°C
1,6-dimethyl-8β-(5-cyano-2-pyrimidino-aminomethyl)-10α-ergoline; m.p. 210°C.

EXAMPLE 9

1,6-dimethyl-8β-(5-nitro-2-pyrimidino-aminomethyl)-10α-methoxyergoline 0.5 g of 2-amino-5-nitropyrimidine was added under stirring and a nitrogen atmosphere to a suspension of 0.168 g of sodium hydride (50% dispersion in mineral oil) in 20 ml of dimethylforamide. When the evaluation of hydrogen ceased, a solution of 1.1 g of 1,6-dimethyl-8β-chloromethyl-10α-methoxyergoline dissolved in 10 ml of dimethylformamide was added and the mixture was heated to 100°C for 4 hours. At the end of the reaction, the dimethylformamide was evaporated off, the mineral oil was removed by treating with n-pentane and the residue was dissolved in boiling ethyl ether and filtered.

The ether was evaporated off and the residue was crystallized from acetone to obtain 0.800 g of the product melting at 160°-162°C.

EXAMPLE 10

1,6-dimethyl-8β-(5-methyl-2-pyrimidino-aminomethyl)-10α-methoxyergoline

To a solution of 0.085 g of sodium amide in 100 ml of liquid ammonia, 0.237 g of 2-amino-5-methylpyrimidine was added with stirring. The ammonia was then slowly evaporated and a solution of 0.554 g of 1,6-dimethyl-8β-chloromethyl-10α-methoxyergoline in 40 ml of anhydrous dimethylsulfoxide was added thereto. The mixture was stirred and heated to 60°C for 30 minutes, after which the dimethylsulfoxide was evaporated off and the residue dissolved in water and chloroform.

The chloroform solution was evaporated and the residue chromatographed on an alumina column. 0.200 g of the product melting at 195°-197°C was obtained.

EXAMPLE 11

1,6-dimethyl-8β -(5-bromo-2-pyrimidino-aminomethyl)-10α-methoxyergoline

By operating in accordance with the procedure described in Example 9, but using 2-amino-5-bromopyrimidine, there was obtained 1,6-dimethyl-8β-(5-bromo-2-pyrimidino-aminomethyl)-10α-methoxyergoline melting at 196°-198°C in 61% yield.

EXAMPLE 12

1,6-dimethyl-8β -(5-cyano-2-pyrimidino-aminomethyl)-10αmethoxyergoline

By operating in accordance with the procedure described in Example 9 but employing 2-amino-5-cyanopyrimidine, there was obtained 1,6-dimethyl-8β -(5-cyano-2-pyrimidino-aminomethyl)-10α-methoxyergoline melting at 136°-138°C in 68% yield.

EXAMPLE 13

1,6-dimethyl-8β -(5-carbethoxy-2-pyrimidino-aminomethyl)-10α-methoxyergoline

By operating in accordance with the procedure described in Example 9, but using 2-amino-5-carbethoxypyrimidine, there was obtained 1,6-dimethyl-8β -(5-carbethoxy-5-pyrimidino-aminomethyl)-10α-methoxyergoline melting at 216°-218°C in 48% yield.

EXAMPLE 14

1,6-dimethyl-8β -(2-pyrimidino-aminomethyl)-10α-methoxyergoline

By operating in accordance with the procedure described in Example 10, using 2-aminopyrimidine, there was obtained 1,6-dimethyl-8β-(2-pyrimidino-aminomethyl)-10α-methoxyergoline melting at 228°-230°C in 35% yield.

EXAMPLE 15

1,6-dimethyl-8β-(5-methoxy-2-pyrimidino-aminomethyl)10α-methoxyergoline

By operating in accordance with the procedure described in Example 10, but using 2-amino-5-methoxy-pyrimidine, there was obtained 1,6-dimethyl-8β-(5-methoxy-2-pyrimidino-aminomethyl)-10 α-methoxyergoline melting at 172°–174°C in 38% yield.

EXAMPLE 16

1,6-dimethyl-8β-(5-methyl-2-pyrimidino-aminomethyl)-10 α-ergoline

By operating in accordance with the procedure described in Example 10, but using 2-amino-5-methyl-pyrimidine and 1,6-dimethyl-8β-chloromethyl-10 α-ergoline, there was obtained 1,6-dimethyl-8β-(5-methyl-2-pyrimidino-aminomethyl)-10α-ergoline melting at 190°-192°C in 63% yield.

Of course, by operating in accordance with the procedures described above, other compounds falling within the scope of the invention, such as 1,6-dimethyl-8β-(5-dimethylamino-2-pyrimidino-aminomethyl)-10α-ergoline and 1,6-dimethyl-8β-(5-acetylamino-2-pyrimidino-aminomethyl)-10α-ergoline can also be prepared.

Variations can, of course, be made without departing from the spirit and scope of the invention.

Having thus described the invention, what is desired to be secured by Letters Patent and hereby claimed is:

1. A compound of the formula:

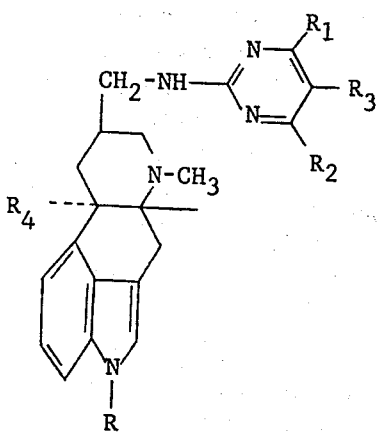

wherein R is selected from the group consisting of hydrogen and methyl; $R_1$ and $R_2$ are independently selected from the group consisting of hydrogen, alkyl having 1 to 6 carbon atoms and phenyl; $R_3$ is selected from the group consisting of hydrogen, halogen, alkyl having 1 to 6 carbon atoms, alkoxy having 1 to 6 carbon atoms, phenyl, cyano, nitro, amino, dimethylamino, and carbalkoxy having 1 to 3 carbon atoms; and $R_4$ is selected from the group consisting of hydrogen and methoxy.

2. The compound of claim 1, which is 1,6-dimethyl-8β-(5-nitro-2-pyrimidino-aminomethyl)-10 α-ergoline.

3. The compond of claim 1, which is 1,6-dimethyl-8β-(4,6-dimethyl-2-pyrimidino-aminomethyl)-10 α-ergoline.

4. The compound of claim 1, which is 1,6-dimethyl-8β -(4-methyl-6-phenyl-2-pyrimidino-aminomethyl)-10α-ergoline.

5. The compound of claim 1, which is 1,6-dimethyl-8β-(5-chloro-2-pyrimidino-aminomethyl)-10 α-ergoline.

6. The compound of claim 1, which is 1,6-dimethyl-8β -(5-amino-2-pyrimidino-aminomethyl)-10 α-ergoline.

7. The compound of claim 1, which is 6-methyl-8β-(5-nitro-2-pyrimidino-aminomethyl)-10 α-ergoline.

8. The compound of claim 1, which is 1,6-dimethyl-8β-(2-pyrimidino-aminomethyl)-10 α-ergoline.

9. The compound of claim 1, which is 1,6-dimethyl-8β-(5-phenyl-2-pyrimidino-aminomethyl)-10 α-ergoline.

10. The compound of claim 1, which is 1,6-dimethyl-8β-(5-dimethylamino-2-pyrimidino-aminomethyl)-10 α-ergoline.

11. The compound of claim 1, which is 1,6-dimethyl-8β-(5-acetylamino-2-pyrimidino-aminomethyl)-10 α-ergoline.

12. The compound of claim 1, which is 1,6-dimethyl-8β-(5-methoxy-2-pyrimidino-aminomethyl)-10 α-ergoline.

13. The compound of claim 1, which is 1,6-dimethyl-8β-(5-cyano-2-pyrimidino-aminomethyl)-10 α-ergoline.

14. The compound of claim 1, which is 1,6-dimethyl-8β-(5-nitro-2-pyrimidino-aminomethyl)-10 α-methoxyergoline.

15. The compound of claim 1, which is 1,6-dimethyl-8β-(5-methyl-2-pyrimidino-aminomethyl)-10 α-methoxyergoline.

16. The compound of claim 1, which is 1,6-dimethyl-8β-(2-pyrimidino-aminomethyl)-10 α-methoxyergoline.

17. The compound of claim 1, which is 1,6-dimethyl-8β-(5-methoxy-2-pyrimidino-aminomethyl)-10 α-methoxyergoline.

18. The compound of claim 1, which is 1,6-dimethyl-8β-(5-bromo-2-pyrimidino-aminomethyl)-10 α-methoxyergoline.

19. The compound of claim 1, which is 1,6-dimethyl-8β-(5-cyano-2-pyrimidino-aminomethyl)-10 α-methoxyergoline.

20. The compound of claim 1, which is 1,6-dimethyl-8β-(5-carbethoxy-2-pyrimidino-aminomethyl)-10 α-methoxyergoline.

21. The compound of claim 1, which is 1,6-dimethyl-8β-(5-methyl-2-pyrimidino-aminomethyl)-10 α-ergoline.

22. The compound of claim 1, which is 1,6-dimethyl-8β-(5-bromo-2-pyrimidino-aminomethyl)-10 α-ergoline.

* * * * *

PO-1050
(5/69)

UNITED STATES PATENT OFFICE
CERTIFICATE OF CORRECTION

Patent No. 3,957,785      Dated May 25, 1976

Inventor(s) GIULIANA ARCARI et al

It is certified that error appears in the above-identified patent and that said Letters Patent are hereby corrected as shown below:

Title page, the title: "Bβ-PYRIMIDINO-AMINOMETHYL-10α-ERGOLINE AND 10α-METHOXYERGOLINE DERIVATIVES" should read -- 8β-PYRIMIDINO-AMINOMETHYL-10α-ERGOLINE AND 10α-METHOXYERGOLINE DERIVATIVES --.

Column 3, line 15: "treating" should read -- treatment --.

Column 4, Table 1, in the heading: "$TC_{50}$" should read -- $IC_{50}$ --.

Columns 5-6, Table 3, column 5, line 2 from the bottom: "80" should read -- 30 --.

Column 6, Table 4, in the heading: "ID" should read -- $ID_{80}$ --; "peros" should read -- per os --.

Columns 7-8, Table 6, column 1, compound 3: "1,6-dimethyl-8β(5-cyano-2-pyrimidino-aminommethyl)-10α-methoxyergoline" should read -- 1,6-dimethyl-8β-(5-cyano-2-pyrimidino-aminomethyl)-10α-methoxyergoline --.

Column 7, line 54: "1,6-dimethyl-8β-guandinomethyl-10β-ergoline" should read -- 1,6-dimethyl-8β-guandinomethyl-10α-ergoline --.

Column 8, line 55: "chloromalondiadehyde" should read -- chloromalondialdehyde --.

PO-1050
(5/69)

UNITED STATES PATENT OFFICE
CERTIFICATE OF CORRECTION

Patent No. 3,957,785                 Dated May 25, 1976

Inventor(s) GIULIANA ARCARI et al

It is certified that error appears in the above-identified patent and that said Letters Patent are hereby corrected as shown below:

Column 9, line 16: "yeild" should read -- yield --;
line 60: "dimethylforamide." should read -- dimethylformamide. --.

Signed and Sealed this

Tenth Day of August 1976

[SEAL]

Attest:

RUTH C. MASON
*Attesting Officer*

C. MARSHALL DANN
*Commissioner of Patents and Trademarks*